(12) United States Patent
Kiraly et al.

(10) Patent No.: US 9,552,672 B2
(45) Date of Patent: Jan. 24, 2017

(54) DYNAMIC GRAPHICAL USER INTERFACES FOR MEDICAL WORKSTATIONS CROSS-REFERENCE TO RELATED APPLICATIONS

(71) Applicant: SIEMENS AKTIENGESELLSCHAFT, München (DE)

(72) Inventors: Atilla Peter Kiraly, Plainsboro, NJ (US); Carol L. Novak, Newtown, PA (US); Benjamin L. Odry, West New York, NJ (US)

(73) Assignee: SIEMENS AKTIENGESELLSCHAFT, München (DE)

( * ) Notice: Subject to any disclaimer, the term of this patent is extended or adjusted under 35 U.S.C. 154(b) by 99 days.

(21) Appl. No.: 14/494,935

(22) Filed: Sep. 24, 2014

(65) Prior Publication Data
US 2015/0009213 A1 Jan. 8, 2015

Related U.S. Application Data

(63) Continuation of application No. 13/226,907, filed on Sep. 7, 2011, now Pat. No. 8,922,546.

(60) Provisional application No. 61/388,185, filed on Sep. 30, 2010.

(51) Int. Cl.
| | |
|---|---|
| *G06T 15/00* | (2011.01) |
| *G09G 5/00* | (2006.01) |
| *G06T 19/00* | (2011.01) |
| *A61B 5/055* | (2006.01) |
| *A61B 6/03* | (2006.01) |
| *A61B 6/00* | (2006.01) |
| *A61B 8/08* | (2006.01) |
| *G09G 5/14* | (2006.01) |

(52) U.S. Cl.
CPC ............ *G06T 19/00* (2013.01); *A61B 5/055* (2013.01); *A61B 6/032* (2013.01); *A61B 6/5241* (2013.01); *A61B 8/5253* (2013.01); *G09G 5/14* (2013.01); *G06T 2219/008* (2013.01); *G09G 2340/12* (2013.01); *G09G 2380/08* (2013.01)

(58) Field of Classification Search
CPC ............ G06T 19/00; G06T 2219/008; G09G 2340/12; G09G 2380/08
See application file for complete search history.

(56) References Cited

U.S. PATENT DOCUMENTS

| | | | |
|---|---|---|---|
| 6,694,163 B1 * | 2/2004 | Vining | G06T 17/00 128/920 |
| 7,627,159 B2 | 12/2009 | Kiraly | |
| 2005/0213849 A1 * | 9/2005 | Kreang-Arekul | G06T 3/4038 382/284 |

(Continued)

OTHER PUBLICATIONS

A.P. Kiraly, G. McLennan, E.A. Hoffman, J.M. Reinhardt, and W.E. Higgins, entitled "Three-dimensional Human Airway Segmentation Methods for Cllinical Virtual Bronchoscopy", Academic Radiology, 2002, pp. 1153-1168.

(Continued)

*Primary Examiner* — Sing-Wai Wu

(57) ABSTRACT

Dynamic systems and methods for depicting context among different views of an imaging visualization application used by a medical workstation are provided.

16 Claims, 6 Drawing Sheets

(56) References Cited

U.S. PATENT DOCUMENTS

2007/0003131 A1* 1/2007 Kaufman ............ G06T 7/0083
382/154
2010/0246957 A1* 9/2010 Visser ................. G06T 19/003
382/173

OTHER PUBLICATIONS

A.P. Kiraly, J.P. Helferty, E.A. Hoffman, G. McLennan, and W.E. Higgins, entitled "Three-dimensional Path Planning for Virtual Bronchoscopy" IEEE Transactions on Medical Imaging, Sep. 2004, pp. 1365-1379, vol. 23, No. 9.
B.L. Odry, A.P. Kiraly, G.G. Slabaugh, C.L. Novak, D.P. Naidich, and J-F. Lerallut, entitled "Active contour approach for accurate quantitative airway analysis", SPIE Medical Imaging 2008, Proceedings of the SPIE, 2008, p. 691613, vol. 6916.
A.P. Kiraly, B.L. Odry, D.P. Naidich, and C.L. Novak, entitled "Boundary-Specific Cost Functions for Quantitative Airway Analysis", Medical Image Computing and Computer Assisted Intervention (MICCAI) 2007, pp. 784-791.
M. Bhalla, N. Turcios, V. Aponte, M. Jenkins, B.S. Leitman, D.I. McCauley, and D.P. Naidich, entitled "Cystic Fibrosis: Scoring System with Thin Section CT", Radiology, 1991, pp. 783, vol. 179.
B.L. Odry, A.P. Kiraly, C.L. Novak, D.P. Naidich, and J-F. Lerallut, entitled "Automated airway evaluation system for multi-slice computed tomography using airway lumen diameter, airway wall thickness and broncho-arterial ratio", Medical Imaging 2006, Proceedings of the SPIE, 2006, pp. 243-253, vol. 6143.
K. Shoemake, entitled "Animating rotation with Quaternion Curves", Proc. ACM SIGGRAPH, Jul. 1985, pp. 245-254, vol. 19.

\* cited by examiner

DYNAMIC GRAPHICAL USER INTERFACES FOR MEDICAL WORKSTATIONS
CROSS-REFERENCE TO RELATED APPLICATIONS

CROSS-REFERENCE TO RELATED APPLICATIONS

This application claims the benefit of U.S. patent application Ser. No. 13/226,907 filed on Sep. 7, 2011, which claims the benefit of Provisional U.S. patent application Ser. No. 61/388,185 filed on Sep. 30, 2010, the disclosures of which are hereby incorporated by reference herein.

TECHNICAL FIELD

The present invention relates to medical imaging workstations. More particularly, the present invention relates to graphical user interfaces for medical workstations.

BACKGROUND

The graphical user interfaces (GUIs) of modem computer systems are software programs that permit users to interact with the systems via graphical images on the system displays. They often depict spatial relationships between conceptual elements using graphical images, such as windows, menus, and dialogs with a dynamic interface. The same is true for windows as they open and close. This trend towards graphical depiction of context is becoming more popular as more powerful Central Processing Units (CPUs) and Graphics Processing Unit (GPUs) become available. These GUIs also distinguish modem computer systems and help provide an improved user experience. In a medical imaging workstation, multiple views of the same dataset are often displayed simultaneously, but little progress has been made in terms of offering dynamic interfaces to provide context.

Many existing visualization methods for medical images are applied directly to the data or some derivative thereof. Although useful, concurrent visualization across different locations and orientations of a workstation display can sometimes be difficult for users to understand. As an example, diseases such as bronchiectasis, asthma, cystic fibrosis and Chronic Obstructive Pulmonary Disease (COPD) are characterized by abnormalities in airway dimensions, including the thickness of the walls and the size of the lumen (i.e., inner airway). Computed Tomography (CT) has become one of the primary means to depict and detect these abnormalities since the availability of high-resolution, near-isotropic data makes it possible to evaluate airways at oblique angles to the scanner plane. Presentation of oblique angles on existing workstations, when allowed, typically involves an interface as depicted in FIG. 1, which shows an example of a medical imaging workstation application for airway analysis. A traditional axial view 2 is shown in the upper left of the figure, along with a 3D view 3 of the segmented airways (upper middle), a cross-sectional view 4 of a selected location (upper right), and a straightened "fillet" view 5 (bottom left) along a selected airway path. All views show portions or derived data from the same 3D volume of the airway tree obtained by the CT imaging scanner. Cross hairs 6 and boxes 7 in the axial view 2 are used to depict a relation or correspondence between the different views.

However, the problem still remains to adequately demonstrate to the user how an oblique plane relates to the rest of the data. This type of visualization is very important to physicians and other health professionals in using a medical imaging workstation, so they can remain confident in the automatic calculation of oblique angles, and remain oriented with respect to the patient's anatomy. Current workstations simply update views with changes in user input, but not much is shown in terms of the direct correspondences between the different views.

SUMMARY

The aforementioned problems are obviated by the present invention which provides a method of visualizing medical images, comprising selecting an anatomical object in a first image and dynamically displaying a predetermined perspective of the anatomical object in a second image that establishes a link to its point of origin in the first image. For example, a series of images illustrates the predetermined perspective transitioning from the selected anatomical object thereby establishing the link to its point of origin in the first image. The dynamically displaying step may comprise overlaying the second image on at least a portion of the first image. The overlaying step may comprise displaying in the second image a series of transitional images of the anatomical object starting with the first image and ending with the second image. Alternatively, the dynamically displaying step may comprise displaying in the second image a series of transitional images of the anatomical object starting with the first image and ending with the second image. The selecting step may comprise selecting the anatomical object in a first or third image and the dynamically displaying step comprises initially overlaying the second image on at least a portion of the first image and moving the second image to stand apart from the first and third images. In such case, the dynamically displaying step may comprise displaying in the second image a series of transitional images of the anatomical object starting with the first image and ending with the second image.

The present invention also provides a method of dynamically visualizing on a medical workstation different views of an image dataset from a 3D volume for an anatomical object, comprising selecting a site on a first global view of the anatomical object displayed by the workstation; selecting a first local view of the anatomical object to be displayed by the workstation; and dynamically displaying the direct correspondences between the two views of the anatomical object. The first global view may be one of either an axial view of the anatomical object or a 3D model view of the anatomical object. The first local view may be a cross-sectional view of the anatomical object. The cross-sectional view may be an oblique cross-sectional view of the anatomical object or a lengthwise cross-sectional view of the anatomical object. The dynamically displaying step may comprise presenting a graphical window containing the first local view that is superimposed on at least a portion of the first global view. Alternatively, the dynamically displaying step may comprise visualizing the origins of the first local view with respect to the first global view. Alternatively, the dynamically displaying step may comprise presenting an animation of images that visualize the direct correspondences between the two views, starting with the first global view, continuing with intermediate views, and ending with the first local view.

The present invention also provides a method of providing dynamic graphical user interfaces for analyzing anatomical airway imaging, comprising selecting a branch of the airway from an axial view of the airway; displaying an image of a cross-section of the selected branch superimposed on the axial view; said image establishing a link to its points of origin in the axial view; and transforming the superimposed image of the cross-section into an image of the cross-section having a desired orientation angle. The method may further comprise displaying the image of the cross-section in a view separate from the axial view and transforming the separate view image of the cross-section into an image of the cross-section having the desired orientation angle at the same time as the superimposed image. The method may further comprise displaying the image of the cross-section in a view separate from the axial view and moving the superimposed image of the cross-section having the desired orientation angle from the axial view so as to replace the separate view image of the cross-section. Also, the transforming step may comprise displaying an animation of successive cross-sections, starting with the cross-section of the selected branch from the axial view, continuing with cross-sections having intermediate orientation angles, and ending with the cross-section having the desired orientation angle. In such case, the method may further comprise displaying the image of the cross-section in a view separate from the axial view and moving the superimposed image of the cross-section having the desired orientation from the axial view so as to replace the separate view image of the cross-section. The desired orientation angle may be oblique or a double oblique angle. In the case of the latter, the displaying an animation step may comprise displaying an animation of successive cross-sections about two axes of the cross-section, starting with the cross-section of the selected branch from the axial view, continuing with cross-sections having intermediate orientation angles in one axis direction and then in a second axis direction, and ending with the cross-section having the desired orientation angle.

The present invention may also provide a method of providing a dynamic graphical user interface for analyzing anatomical airway imaging, comprising selecting an airway path of the airway from one of either an axial view or a 3D tree model view of the airway as the origin view; and dynamically displaying an image of a lengthwise cross-section of the selected airway path, said image establishing a link to its points of origin in the origin view. The dynamically displaying step may comprise transforming the selected airway path into the image of the lengthwise cross-section. The dynamically displaying step may comprise transforming the selected airway path into the image of the lengthwise cross-section and displaying an image of the lengthwise cross-section in a view separate from the origin view. In such case, the transforming step may comprise displaying a series of transitional images that unfold the selected airway path into the image of the lengthwise cross-section.

The present invention may also provide a system for visualizing medical images, comprising an imager that acquires image data of anatomical structures and a processor that manipulates the acquired image data and stored image data to select an anatomical object in a first image and dynamically display a predetermined perspective of the anatomical object in a second image that establishes a link to its points of origin in the first image.

BRIEF DESCRIPTION OF THE DRAWINGS

FIG. 4 is a photograph of a first visualization of a medical imaging workstation application for airway analysis that implements the method of FIG. 3a.

DETAILED DESCRIPTION

Figure 2:
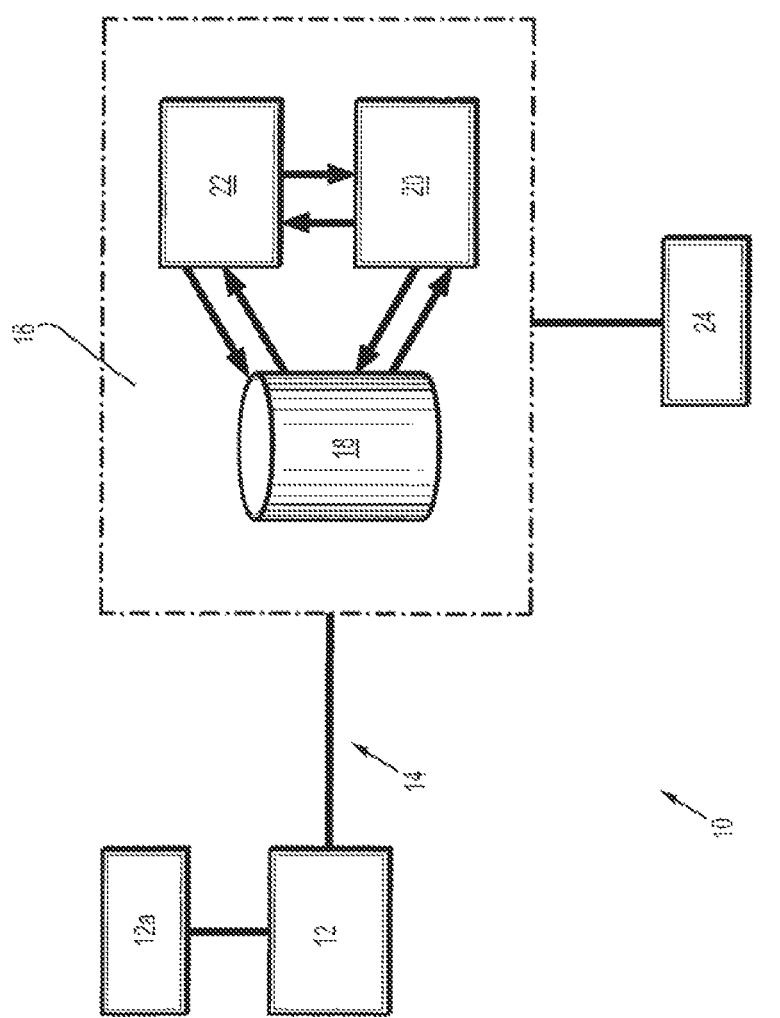
FIG. 2 a block diagram of a medical imaging system (simplified) that is operable in accordance with the present invention.

FIG. 2 is a block diagram of a medical imaging system 10 (simplified) that is operable in accordance with the present invention. The system 10 comprises a medical imaging scanner 12 that acquires image data of the anatomical region of interest of a patient under examination and, more particularly in this case, the airways of the patient. As noted above, the scanner 12 may use computed tomography (CT) imaging which has become one of the primary means to examine abnormalities of airways. However, the scanner 12 may use any other appropriate imaging modality to acquire 3D image data, for example, magnetic resonance, ultrasound, and nuclear medicine imaging. The scanner 12 may acquire raw image data from multiple scanned views of the anatomical region of interest, reconstruct the images, and produce an image volume. The image data signals may be in Digital Imaging and Communications in Medicine (DICOM) format. Other formats may also be used.

The imaging scanner 12 is operably connected to a computer system 12a that controls the operation of the scanner 12 and, via a communication channel 14, to an image processing system 16 that processes the image data signals utilizing appropriate image processing software applications. The image processing system 16 typically has an image data archive or database 18, an application server 20, and a user workstation 22. The components of the image processing system 16 are interconnected via a communications network that may be implemented by physical connections, wireless communications, or a combination. The image data archive or database 18 is adapted to store the image data signals that are produced by the image scanner 12 as well as the results of any additional operations on the image datasets by the other components of the image processing system 16. The image data archive or database 18 may be a Picture Archiving and Communications System (PACS). Other types of image data archives or databases may also be used.

The user workstation 22 is adapted to control the operation of the imaging processing system 16 and its various components. The user workstation 22 particularly operates the application server 20 and the various image processing software applications that are stored in, or are accessible by, the server 20. The application server 20 also manages and coordinates the image datasets among the image processing applications. The image processing applications may include, for example, visualizations, computer-aided diagnosis (CAD), medical image rendering, anatomical segmentation, or any other type of medical image processing application. The image processing applications may also include methods implemented according to the present invention. The image data archive or database 18, applications server 20, and the user workstation may also each be connected to a remote computer network 24 for communication purposes or to access additional data or functionality. The workstation 22 may comprise appropriate user interfaces, like displays, storage media, input/output devices, etc. In some configurations, the methods implemented according to the present invention may be directly stored in, or are accessible by, the user workstation 22 and the associated display or other user interface.

The various components of the imaging system 10 are conventional and well known components. They may be configured and interconnected in various ways as necessary or as desired. The imaging system 10 and, in particular, the image processing system 16 is adapted to permit the imaging system 10 to operate and to implement methods in accordance with the present invention, for example, as shown in FIGS. 3a and 3b.

Figure 3A:
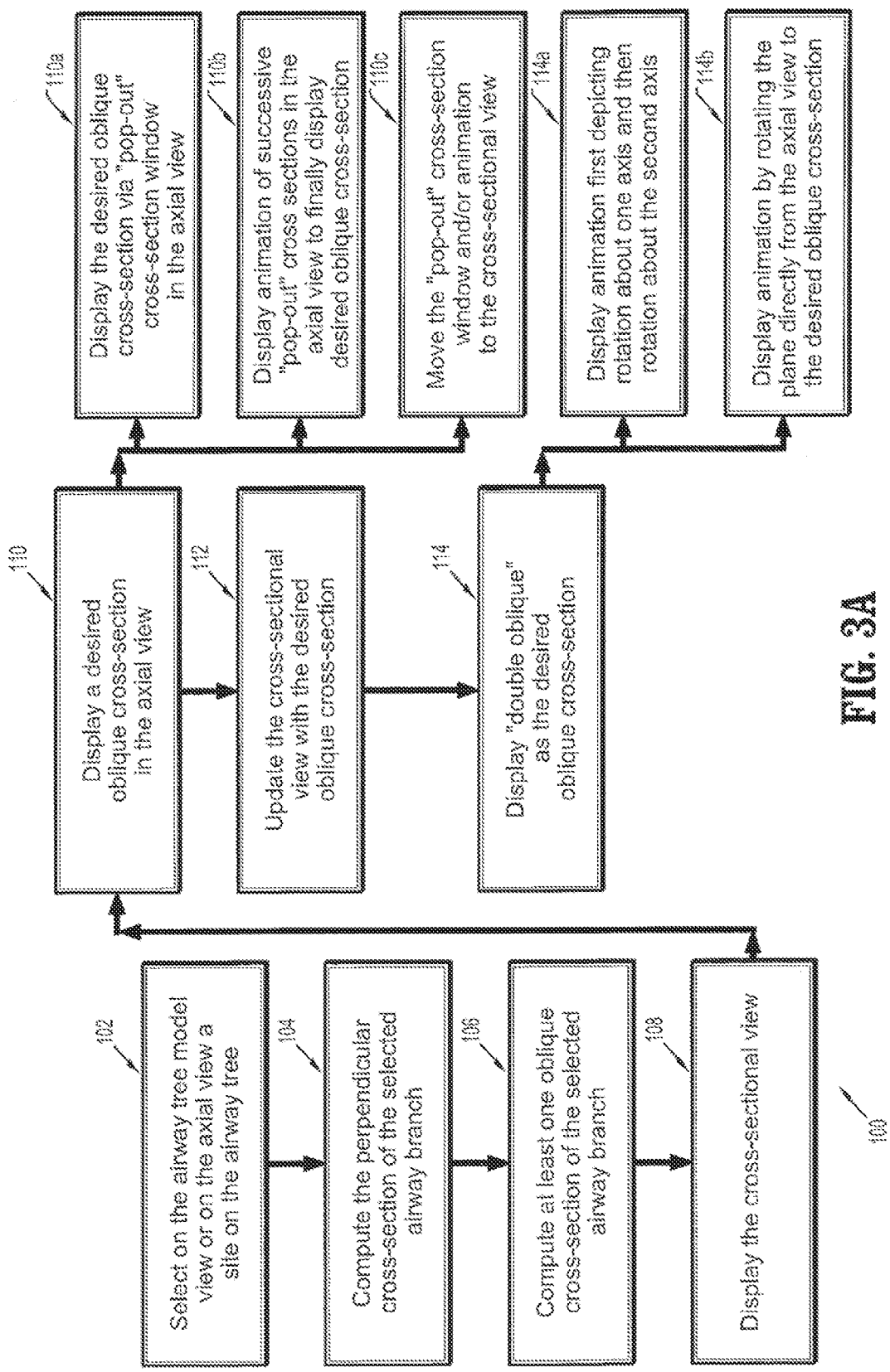
FIG. 3a is a block diagram of a method of dynamically presenting different image views of a medical image dataset in accordance with the present invention.
Figure 3B:
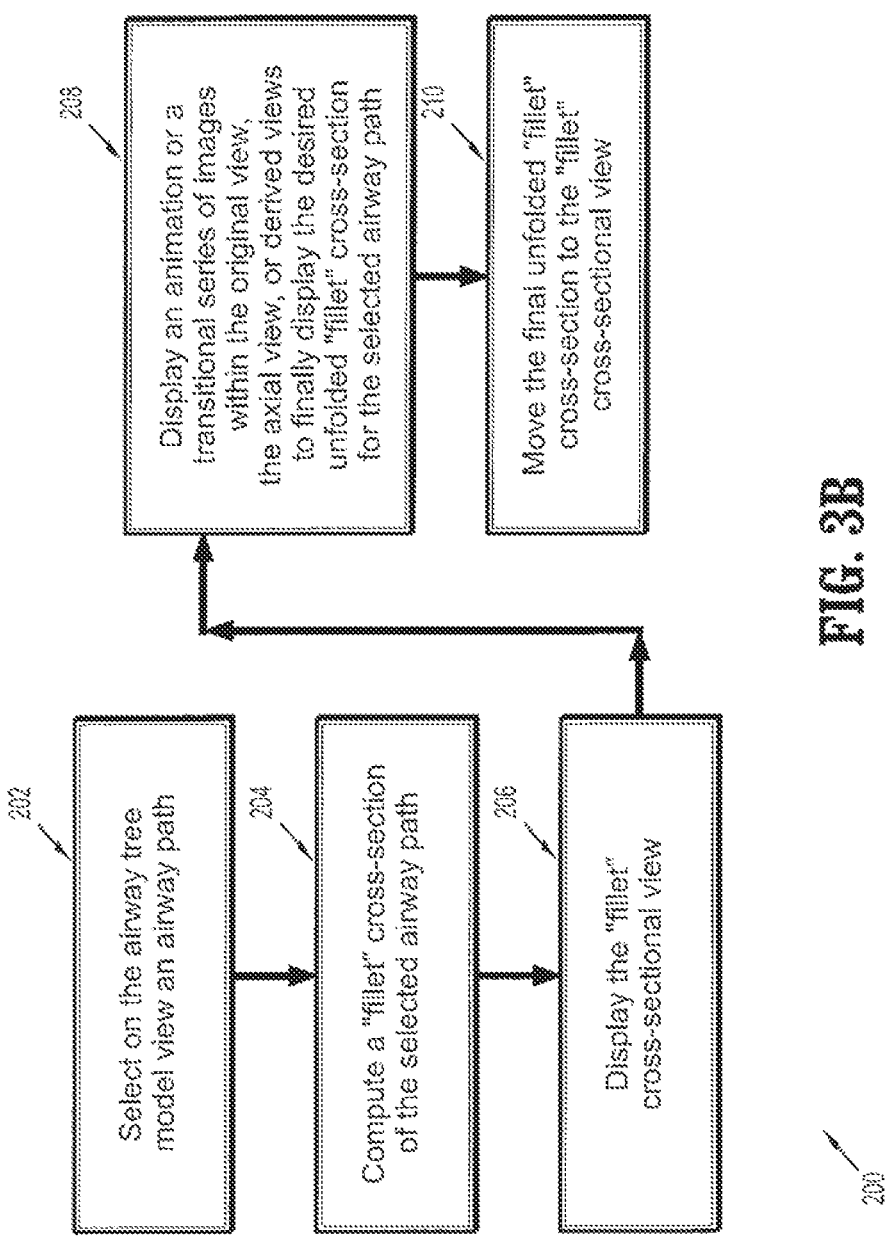
FIG. 3b is a block diagram of a second method of presenting different image views of a medical image dataset in accordance with the present invention.

FIGS. 3a and 3b are block diagrams of respective methods 100, 200 of dynamically presenting different image views of a medical image dataset in accordance with the present invention. The dynamic interfaces and visualizations provided by the methods 100, 200 allow for improved user experiences, specifically allowing system 10 users to better understand correspondences between different views of a dataset. The methods 100, 200 are each particularly described for the visualization of the analysis of a patient's airway but are each also applicable to other medical analyses and other anatomical areas of interest, for example, blood vessels. Also, the methods 100, 200 are described in terms of CT imaging but are also applicable to other imaging modalities such as Magnetic Resonance (MR) imaging as well as visualization methods involving the unfolding of different anatomical structures such as the ribs.

Prior to carrying out the methods 100, 200 for an airway analysis application, a system 10 user generally carries out steps to extract an airway tree from the CT image dataset of a patient obtained at specific time-point. Using, for example, the imaging system 10 described above, an image of an original CT volume of a patient's airway tree is obtained. The image may be obtained in various ways, such as, directly subsequent to a CT scan of the patient; from the image data archive or database 18; or from the remote computer network 24. The imaging system 10 typically processes the image of the original CT volume and obtains an airway segmentation image from the image of the original CT volume. There are several known methods for performing an airway segmentation and, thus, extracting the airway or bronchial tree from the CT dataset.

From the airway segmentation image (i.e., the segmented bronchial tree), the system 10 creates an airway tree model with a hierarchy that represents the bronchial generations. This permits physicians and other health professionals to select specific airways for review and evaluation. The creation of the airway tree model may be accomplished by performing a skeletonization of the airway segmentation image. In brief, skeletonization is a process for reducing foreground image data in an image to a skeletal remnant that preserves the extent and connectivity of the original image. The result is a hierarchical description of the airway tree as a connected series of branches. The hierarchical description identifies for each branch, from which parent branch it is descended, and which child branches are descended from it. The description also contains a generation number, for example, starting with 0 for the trachea, 1 for the left and right main bronchi, 2 for the lobar branches, 3 for the segmental branches, 4 for the sub-segmental branches, and so forth. Each branch is described by a series of sites. In addition to containing positional information, each site also contains orientation information of the branch at that point. There are several known methods for skeletonizing an airway segmentation to create an airway tree model.

Figure 1:
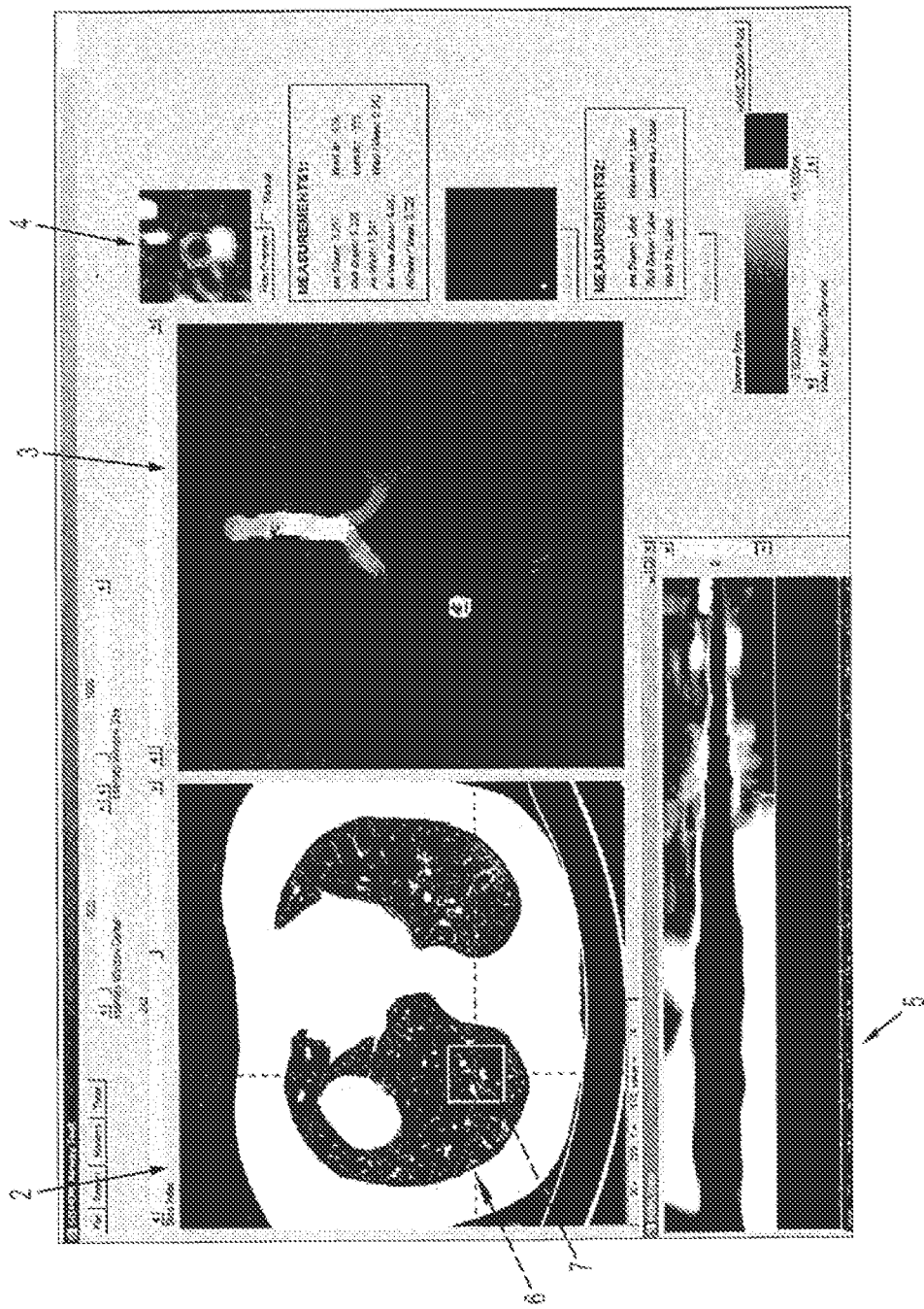
FIG. 1 is a photograph of a typical visualization of a medical imaging workstation application for airway analysis.

The tree model permits the airway branches of interest to be viewed and identified more easily by a system 10 user. Also, as noted above, the tree model provides information that determines the center and orientation for each airway branch. This information can be used by the imaging system 10 to determine cross-sectional views (e.g., cross-sections perpendicular to the branch) at any point, particularly the center point, within an airway branch for performing airway quantification, i.e., the evaluation of airway dimensions, for an airway branch. A system 10 user may then visualize the airway in different views/viewing panes using a display of the workstation 22. A standard visualization is shown in FIG. 1 described above.

With the present invention, a system 10 user may instead dynamically display different views from the image dataset of the 3D volume of the airway tree obtained by the imaging system 10. More specifically, each of the methods 100, 200 of the present invention provide a dynamic interface for the presentation of the different image views within the dataset. As will be made evident, the dynamic GUI and GUI elements establish context between the different views of the same volume and derived data.

Figure 4:
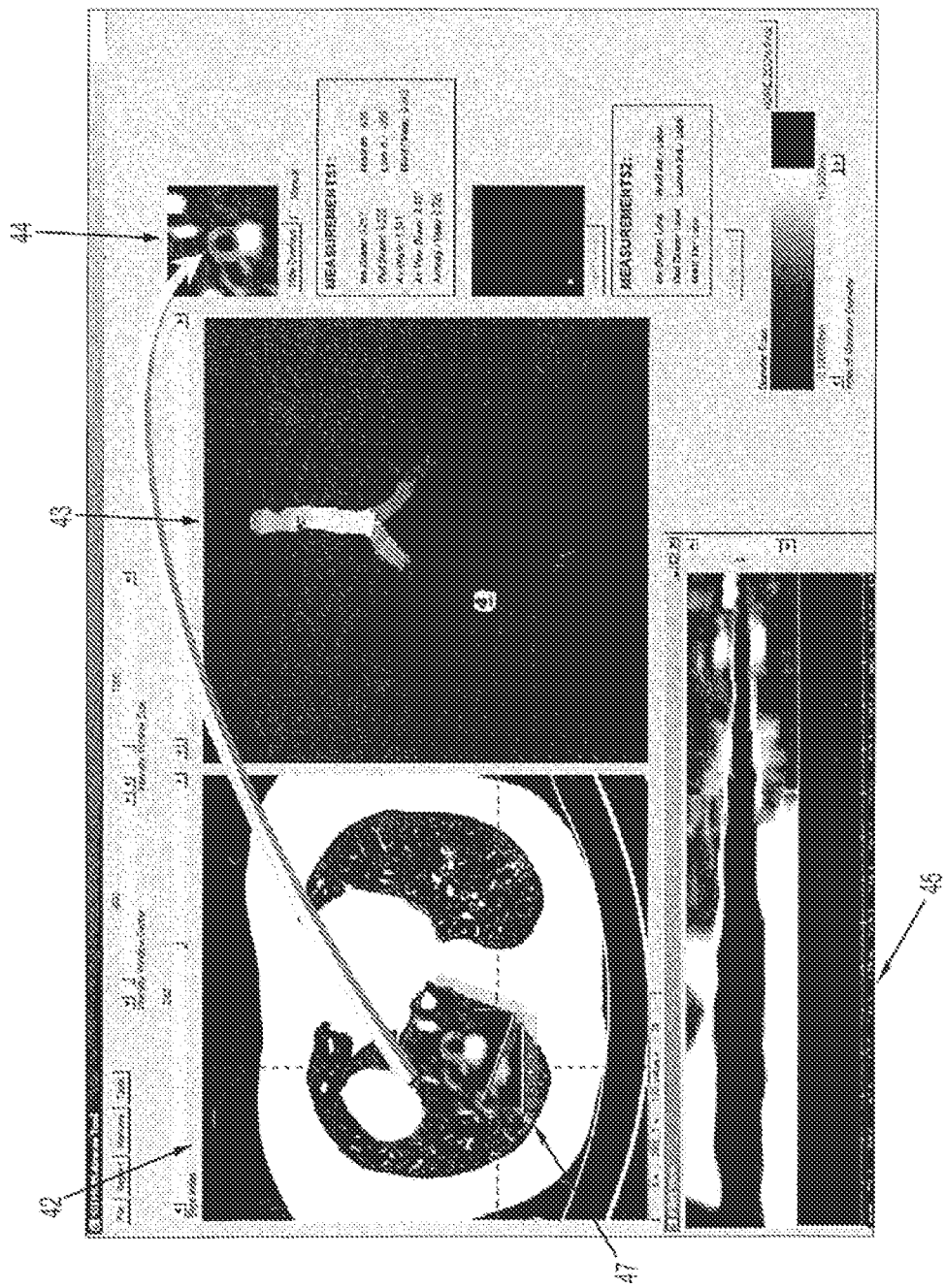

In describing the method 100 for the case of cross-sectional views and curved planar image reformations, reference is also made to FIG. 4 which is a visualization of a medical imaging workstation application for airway analysis that implements the method 100. Similar to FIG. 1, the figure shows several, different views/viewing panes: an axial view 42 of the airway tree, a 3D view 43 of the segmented airway (i.e. the airway tree model view), a cross-sectional view 44 of a selected branch location, and a straightened "fillet" view 45 along a selected airway path. As will be described in detail below, the method 100 presents the cross section view 44 by a dynamic change of view within the axial image 42 and shows both location and orientation with respect to the axial view 42. This established context can make it easier for the system 10 user to appreciate the relation of views with respect to each other.

For the example of an airway analysis application, a cross-sectional view of an airway branch is often desired, even though airways frequently lie obliquely to the scanned volume. Generally, the method 100 provides that, once an airway branch is selected from the standard (e.g. axial) view 42, the cross-section of the branch will "pop out" of the axial view 42 and rotate to its orientation (at some angle), while the separate cross-sectional view 44 will continually update as the orientation is changed by the system 10. In this context, the term "pop out" means that a graphical window or box containing the cross-section, or other structure, is displayed over or within a view/viewing pane, such as the axial view 42.

More particularly, the user workstation 22 will typically display global views of the airway tree, i.e., the axial view 42 and the airway tree model view 43, at the start of operation. The method 100 permits a user to either select (e.g., via a computer mouse point and click operation) on the airway tree model view 43 or directly on the axial slice 42 to select a site on the airway tree (Step 102). The system 10 computes the perpendicular cross section of the selected airway branch (Step 104) using details of the airway tree model in a manual operation or using a "click anywhere" approach which provides an automatic calculation from already-detected and stored details of the branch, both of which supply a site location and direction. The directional data indicates the direction or orientation of the airway branch to obtain an oblique cross section. The system 10 may then compute at least one oblique cross-section using this information (Step 106).

Following the site selection and the different cross-section computations, instead of simply displaying the cross section as in FIG. 1 (Step 108), the method 100 may provide the "pop-out" cross-section window described above (Step 110a) or an animation 47 of successive "pop-out" cross sections, for example, beginning with a cross-section identical to the original axial view 42, and ending with a view of the desired oblique MPR (multi-planar reconstruction) (Step 110b). Multi-planar reconstruction is a post-image processing technique commonly used by an imaging system 10 to reconstruct a slice in any position and orientation through the obtained 3D volume. MPR can reconstruct axial images into coronal, sagittal and oblique anatomical planes but can also specify a plane off an oblique image. Intervening frames in the animation 47 show intermediate angles of obliqueness. The resulting animation 47 appears much like a "swinging door" opening up within the axial slice 42, with continual updates of the cross section as its orientation angle changes. In both cases, the corresponding cross-sectional view 44 may also be updated in the same manner (Step 112). Alternatively, the method 100 may display the "pop out" cross-section window at the axial view 42 and "move the cross section" (i.e. re-display the cross-section at a series of locations across the display to shift the cross-section from a start location to an end location on the display into the top right cross-sectional viewing pane 44 as suggested by the arrow in FIG. 4 (Step 110c).

In many cases, the desired oblique MPR will be "double oblique", i.e. require rotation about two axes with respect to the original (axial or tree model) view (Step 114). In this case, in one embodiment of the invention, the animation may first depict rotation about one axis and then illustrate rotation about the second axis (Step 114a). This may be accomplished by always rotating about the X-axis first and then rotating about the Y-axis, or by always performing the largest of the two component rotations first. In a second embodiment of the invention, the animation may be performed by rotating the plane directly from the original (axial or tree model) view to the desired oblique MPR (Step 114b) as can be done by use of SLERP (Spherical Linear intERPolation) to interpolate between two quaternions representing the viewing direction. As these changes in viewing direction occur, a 3D cross-section window "pop-out" can be continually updated to reflect the change in the cross-sectional data as well as its border positions with regard to the original view, e.g., axial view 42.

The following generally describes mathematically the dynamic process implemented by the imaging system 10 for the case of the branch cross-section described above. The selected site may be represented as $s=(x, d)$ where x is a 3D location (x, y, z) within the image and $d=(X, Y, Z, W)$ may be a quaternion implicitly containing the viewing direction. The default viewing quaternion for the axial plane (towards the patient head) may be represented as $d_A$. The viewing direction for the time frame of the dynamic sequence $t=[0,1]$, with 1 being the end of the dynamic sequence, may be determined by $d_{dynamic}=\text{Slerp}(d_A, d; t)$ where t=1 results in the final viewing direction of d. This process allows for a smooth transition from the axial viewing direction to that of the computed viewing direction for the site. As each viewing direction is updated, the cross-section is updated as well along with possibly an embedded 3D plane within the axial image 42 to establish the shift from the axial plane to the oblique plane of the airway. This dynamic update of the cross-section can also be accompanied by a physical shift of the cross-section to its top right location 44 within the application as shown in FIG. 4. Adjustments in transparency of the "pop-out" cross-section window within the axial slice 42 would also be possible. Finally, with the increasing availability of 3D displays, the "pop-out" cross-section window can be displayed in 3D as it is moving out of the axial plane.

The present invention provides another method 200 for the case of a length-wise or "fillet" cross section of the airway. This is described with reference to FIG. 5 which is a visualization of a medical imaging workstation application for airway analysis that implements the method 200. Similar to FIG. 4, the figure shows several, different views/viewing panes: an axial view 52 of the airway tree, a 3D view 53 of the segmented airway (i.e. the airway tree model view), a cross-sectional view 54 of a selected branch location, and a straightened "fillet" view 55 along a selected airway path. As will be described in detail below, the method 200 presents the "fillet" cross section view 55 by a dynamic change of view within the airway tree model view 43, specifically, an unfolded view of an airway.

More particularly, the method 200 permits a user to select on the airway tree model view 53 an airway path, i.e., a series of consecutive branches that form a continuous path in the airway tree (Step 202). The sites along the path are straightened by the system 10 into a "fillet" cross-sectional view 55 as shown in the bottom left of FIG. 5 (Step 204). Following the site selection, instead of simply displaying the computed "fillet" view 55 (Step 206), the method 100 also shows an animation or a transitional series of images in order to establish the points of origin within the original view 53, the axial view 52, or derived views (Step 208). In this case, the airway path within the tree model view 53 is transformed, via the transitional image series, into the "fillet" view 55 in the lower left hand side of FIG. 5. In this way, the "fillet" view 55 unfolds from the 3D tree model view 53 and drops onto the bottom viewing pane 55 through a dynamic animation sequence (Step 210). This presentation allows the user to more intuitively comprehend the visualization as well as the points within the dataset that are used to derive the views.

Figure 5:
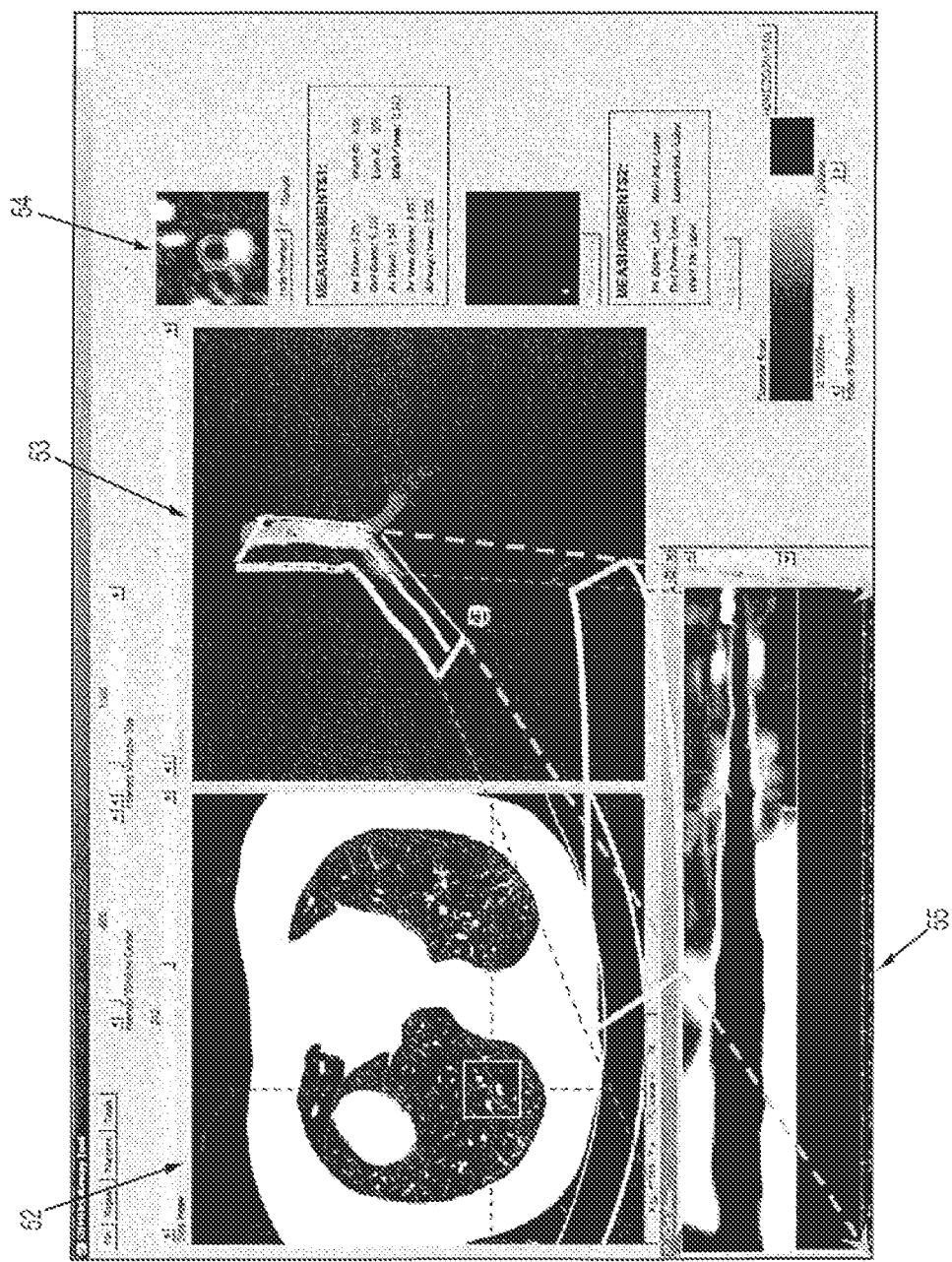
FIG. 5 is a photograph of a visualization of a medical imaging workstation application for airway analysis that implements the method of FIG. 3b.

The following generally summarizes mathematically how to accomplish the above dynamic process implemented by the imaging system 10 for the case of the "fillet" cross-section described above. With the straightened "fillet" view 55 being comprised of a series of n sites $S=\{S_1, S_2 \ldots S_n\}$, the fillet view 55 is computed and unchanged. However, a 3D surface is created to which this image is projected upon Again, the dynamic sequence is completed in time $t=[0,1]$. During this time frame, the shape of the 3D surface is continually changed from its original 3D location (in the tree model view 53) to the flat location (in the "fillet" view 55) within the display as shown in FIG. 5. This surface can be computed by using the site directions and relative locations. A plane can be defined based on the locations and directions of each site. Alone they form a 3D string of points, but extending each point perpendicular to their direction allows a 3D plane to be defined. This exact same process is used to choose points for rendering the "fillet" view 55. This process is used to compute and display the initial 3D plane for the tree model view 53 and, then, the final 2D plane for the "fillet" view 55 can be computed by setting all of the directions to the same quaternion. Again, a SLERP function can be used to smoothly transform the directions to result in a final 2D surface. The position of this surface can also be updated (i.e., moved) to the correct display viewing area. This is also shown in FIG. 5 by the outline and the dotted arrows.

These improved interface mechanisms require the ability to quickly compute cross-sections in real-time as well as display dynamic overlays with varying levels of transparency and three dimensionality. The computing power of available modern workstations easily meets the requirements for these capabilities.

Advantageously, the present invention provides a dynamic approach to establish context between different views of a 3D volume within a medical workstation. A dynamic flow of information between different views allows for an improved user experience by offering more intuitive understanding of the contextual relationship between different views. Also, the present invention may be used for different applications, such as the method 100 for cross-sections and for curved planar reformations described above that reveal the origins of the visualization with respect to the original volume data. Further, medical workstations using advanced dynamic GUIs for updating views can quickly distinguish themselves from existing platforms, much like more modern operating systems make use of new GUIs to distinguish themselves from their predecessors.

Other modifications are possible within the scope of the invention. For example, the subject patient to be scanned may be a human subject, animal subject or any other suitable object. Also, although the steps of the methods 100, 200 have been described in a specific sequence, the order of the steps may be re-ordered in part or in whole and the steps may be modified, supplemented, or omitted as appropriate. Also, the methods 100, 200 may use various well known algorithms and software applications to implement the steps and substeps. Further, the methods 100, 200 may be implemented in a variety of algorithms and software applications. Further, the methods 100, 200 may be supplemented by additional steps or techniques. It is also understood that the methods 100, 200 may carry out all or any of the steps using real-time data, stored data from the image data archive or database 18, data from a remote computer network 24, or a mix of data sources.

Also, the various components of the imaging system 10 are conventional and well known components. They may be configured and interconnected in various ways as necessary or as desired. Further, although in the described methods 100, 200 the health professional may use self-contained imaging instrumentation and tools, the health professional may use other instrumentation or tools in combination with or in place of the imaging instrumentation and tools described for any step or all the steps of the methods 100, 200, including those that may be made available via telecommunication means. Further, the described methods 100, 200, or any steps, may be carried out automatically by appropriate imaging instrumentation and tools or with some manual intervention.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof.

It should be noted that the term "comprising" does not exclude other elements or steps and the use of articles "a" or "an" does not exclude a plurality. Additionally, the steps of various methods disclosed herein are not required to be performed in the particular order recited, unless otherwise expressly stated.

We claim:

1. A method, comprising:
providing a first image;
selecting an anatomical object in the first image;
overlaying a second image on at least a portion of the first image to create a series of images transitioning between the first image and a predetermined perspective of the anatomical object in the second image; and
displaying the series of images such that the predetermined perspective of the anatomical object establishes a link to its origin in the first image.

2. The method of claim 1 further comprising a third image, and wherein the selecting step comprises selecting the anatomical object in the first or third image, and wherein the overlaying step comprises overlaying the second image on at least a portion of the first image and moving the second image to stand apart from the first and third images.

3. The method of claim 2, wherein the displaying step comprises displaying the series of images in the second image, starting with the first image and ending with the second image.

4. The method of claim 1, wherein the series of images are displayed in the second image starting with the first image and ending with the second image.

5. A method of visualizing on a medical workstation different views of an image dataset from a 3D volume for an anatomical object, comprising:
selecting a site on a first global view of the anatomical object displayed by the workstation;
selecting a first local view of the anatomical object to be displayed by the workstation;
superimposing the first local view on at least a portion of the first global view to create a series of images transitioning between the first global view and the first local view; and
displaying the series of images via a graphical window containing the first local view that is superimposed on at least a portion of the first global view.

6. The method of claim 5, wherein the first global view is one of either an axial view of the anatomical object or a 3D model view of the anatomical object.

7. The method of claim 5, wherein the first local view is a cross-sectional view of the anatomical object.

8. The method of claim 7, wherein the cross-sectional view is an oblique cross-sectional view of the anatomical object.

9. The method of claim 7, wherein the cross-sectional view is a lengthwise cross-sectional view of the anatomical object.

10. The method of claim 5, wherein the transition between the two views begins with visualizing the origins of the first local view with respect to the first global view.

11. The method of claim 5, wherein the series of images present an animation of images starting with the first global view, continuing with intermediate views, and ending with the first local view.

12. A method of providing a dynamic graphical user interface for analyzing anatomical airway imaging, comprising:
selecting an airway path of the airway from one of either an axial view or a 3D tree model view of the airway as the origin view, the airway path comprised of a series of consecutive branches that form a continuous path;

straightening the consecutive branches along the continuous path into a length-wise cross-sectional view of the selected airway path to create a series of views transitioning between the origin view and an image of the lengthwise cross-section; and displaying the series of views such that the image of the lengthwise cross-section establishes a link to its point of origin in the origin view.

13. The method of claim 12, wherein the displaying step comprises transforming the selected airway path into the image of the lengthwise cross-section.

14. The method of claim 12, wherein the displaying step comprises transforming the selected airway path into the image of the lengthwise cross-section and displaying an image of the lengthwise cross-section in a view separate from the origin view.

15. The method of claim 14, wherein the transforming step comprises displaying a series of transitional images that unfold the selected airway path into the image of the lengthwise cross-section.

16. A system comprising:
an image database;
an imager configured to acquire and store image data of anatomical structures in the image database;
a processor connected to the image database and configured to manipulate the image data in response to a selection of an anatomical object of a first image of the image data by creating a series of transitional images between the first image and a predetermined perspective of the anatomical object in a second image, the series of transitional images establishing a link to the predetermined perspective point of origin in the first image; and
displaying the series of transitional images via a display.

* * * * *